US009095654B2

United States Patent
Schwab et al.

(10) Patent No.: US 9,095,654 B2
(45) Date of Patent: Aug. 4, 2015

(54) SYRINGE FOR MIXING AND DISPENSING ADIPOSE TISSUE

(71) Applicant: Allergan, Inc., Irvine, CA (US)

(72) Inventors: Justin Schwab, Santa Barbara, CA (US); Edwin Kayda, Santa Barbara, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/966,953

(22) Filed: Aug. 14, 2013

(65) Prior Publication Data

US 2014/0052059 A1 Feb. 20, 2014

Related U.S. Application Data

(60) Provisional application No. 61/683,157, filed on Aug. 14, 2012.

(51) Int. Cl.
*A61M 5/00* (2006.01)
*A61M 5/19* (2006.01)
(Continued)

(52) U.S. Cl.
CPC ................. *A61M 5/19* (2013.01); *A61M 5/315* (2013.01); *A61M 5/50* (2013.01);
(Continued)

(58) Field of Classification Search
CPC . A61M 3/005; A61M 5/2066; A61M 5/2448; A61M 5/284; A61M 5/31596; A61M 5/3294; A61M 2005/2448; A61M 2005/2451; A61M 2005/31596; A61M 2005/2414; A61M 2005/3128; A61M 2202/0021; A61M 2202/08; A61M 2205/276; F16K 1/16; F16K 1/165; F16K 1/2092; F16K 1/2285; F16K 1/24; F16K 15/038; F16K 17/02; F16K 35/00; F16K 99/0059; A51M 5/19; A51M 5/315; A51M 5/50
USPC ............... 604/82, 83, 84, 181, 187, 191, 518; 222/129.2, 145.1–145.7; 137/602, 605, 137/896
See application file for complete search history.

(56) References Cited

U.S. PATENT DOCUMENTS 2,737,946 A 3/1956 Hein, Jr.
2,853,070 A 9/1958 Maurice
(Continued)

FOREIGN PATENT DOCUMENTS

EP 0362484 4/1990
EP 1051988 11/2000
(Continued)

OTHER PUBLICATIONS

Davidenko et al., "Collagen-hyaluronic acid scaffolds for adipose tissue engineering", ACTA Biomaterialia, vol. 6, No. 10, Oct. 1, 2010, pp. 3957-3968, XP055055114.
(Continued)

*Primary Examiner* — Bhisma Mehta
*Assistant Examiner* — Nicholas Meghri
(74) *Attorney, Agent, or Firm* — Linda Allyson Nassif

(57) ABSTRACT

A device is provided for introducing into a patient a combination of adipose tissue and an additive, for example, a hydrogel additive. The device includes a fat cartridge, an additive cartridge containing an additive, and a housing configured to receive, in a side-by-side manner, the fat cartridge and additive cartridge. A mixing tip may be included for causing mixing of the cartridge components prior to extrusion from a needle or cannula.

9 Claims, 6 Drawing Sheets

(51) Int. Cl.
    *A61M 5/315* (2006.01)
    *A61M 5/50* (2006.01)
    *A61M 5/24* (2006.01)
    *A61M 5/31* (2006.01)

(52) U.S. Cl.
    CPC .............. *A61M 2005/2414* (2013.01); *A61M 2005/3128* (2013.01); *A61M 2202/0021* (2013.01); *A61M 2202/08* (2013.01); *A61M 2205/276* (2013.01)

(56) References Cited

U.S. PATENT DOCUMENTS

| | | | |
|---|---|---|---|
| D202,754 S | 11/1965 | Naftolin | |
| D214,112 S | 5/1969 | Langdon | |
| D224,066 S | 6/1972 | McDonald | |
| 3,720,211 A | 3/1973 | Kyrias | |
| 3,767,085 A * | 10/1973 | Cannon et al. | 222/82 |
| 3,807,048 A | 4/1974 | Malmin | |
| 4,240,423 A | 12/1980 | Akhavi | |
| 4,240,426 A | 12/1980 | Akhavi | |
| 4,273,122 A | 6/1981 | Whitney et al. | |
| 4,326,517 A | 4/1982 | Whitney et al. | |
| 4,529,401 A | 7/1985 | Leslie et al. | |
| 4,699,612 A | 10/1987 | Hamacher | |
| D303,010 S | 8/1989 | Jabbusch | |
| 4,869,717 A | 9/1989 | Adair | |
| 5,024,656 A | 6/1991 | Gasaway et al. | |
| 5,046,506 A | 9/1991 | Singer | |
| 5,100,390 A | 3/1992 | Lubeck et al. | |
| 5,104,375 A * | 4/1992 | Wolf et al. | 604/518 |
| 5,127,436 A | 7/1992 | Campion et al. | |
| 5,141,496 A | 8/1992 | Dalto et al. | |
| 5,295,980 A | 3/1994 | Ersek | |
| 5,305,788 A | 4/1994 | Mayeux | |
| 5,322,511 A | 6/1994 | Armbruster et al. | |
| 5,344,407 A | 9/1994 | Ryan | |
| 5,383,851 A | 1/1995 | Mackinnon, Jr. et al. | |
| 5,405,330 A | 4/1995 | Zunitch et al. | |
| D378,939 S | 4/1997 | Smith et al. | |
| 5,690,618 A | 11/1997 | Smith et al. | |
| 5,817,033 A | 10/1998 | DeSantis et al. | |
| D424,194 S | 5/2000 | Holdaway et al. | |
| D441,077 S | 4/2001 | Garito et al. | |
| 6,231,552 B1 | 5/2001 | Jentzen | |
| 6,432,046 B1 | 8/2002 | Yarush et al. | |
| 6,613,010 B2 | 9/2003 | Castellano | |
| 6,616,448 B2 | 9/2003 | Friedman | |
| D483,116 S | 12/2003 | Castellano | |
| 6,689,095 B1 | 2/2004 | Garitano et al. | |
| 6,783,514 B2 | 8/2004 | Tovey et al. | |
| 6,824,526 B2 | 11/2004 | Castellano | |
| 7,018,356 B2 | 3/2006 | Wise et al. | |
| 7,419,472 B2 | 9/2008 | Hibner et al. | |
| 7,494,473 B2 | 2/2009 | Eggers et al. | |
| D615,192 S | 5/2010 | Mudd et al. | |
| 7,878,981 B2 | 2/2011 | Strother et al. | |
| D637,287 S | 5/2011 | Mudd et al. | |
| 8,029,460 B2 | 10/2011 | Rush et al. | |
| 8,066,629 B2 | 11/2011 | Dlugos | |
| 8,480,630 B2 | 7/2013 | Mudd et al. | |
| 8,603,028 B2 | 12/2013 | Mudd et al. | |
| 2002/0010433 A1 | 1/2002 | Johnson et al. | |
| 2002/0151843 A1 | 10/2002 | Correa et al. | |
| 2003/0144632 A1 | 7/2003 | Hommann et al. | |
| 2003/0199883 A1 | 10/2003 | Laks | |
| 2004/0092927 A1 | 5/2004 | Podhajsky et al. | |
| 2004/0147883 A1 | 7/2004 | Tsai | |
| 2005/0085767 A1 | 4/2005 | Menassa | |
| 2005/0131353 A1 | 6/2005 | Mossanen-Shams et al. | |
| 2005/0137496 A1 | 6/2005 | Walsh et al. | |
| 2005/0261633 A1 | 11/2005 | Khalaj | |
| 2006/0079765 A1 | 4/2006 | Neer | |
| 2006/0089594 A1 | 4/2006 | Landau | |
| 2007/0083155 A1 | 4/2007 | Muller | |
| 2007/0100363 A1 | 5/2007 | Dollar et al. | |
| 2007/0212385 A1 | 9/2007 | David | |
| 2007/0250010 A1 | 10/2007 | Hohlfelder et al. | |
| 2008/0033347 A1 | 2/2008 | D'Arrigo et al. | |
| 2008/0071385 A1 * | 3/2008 | Binette et al. | 623/23.72 |
| 2008/0097325 A1 | 4/2008 | Tanaka et al. | |
| 2008/0108952 A1 | 5/2008 | Horvath et al. | |
| 2008/0188816 A1 | 8/2008 | Shimazaki et al. | |
| 2008/0200758 A1 | 8/2008 | Orbay et al. | |
| 2009/0088703 A1 | 4/2009 | Azar | |
| 2009/0124996 A1 | 5/2009 | Heneveld et al. | |
| 2009/0143746 A1 | 6/2009 | Mudd et al. | |
| 2009/0240200 A1 | 9/2009 | Heneveld et al. | |
| 2009/0299328 A1 | 12/2009 | Mudd et al. | |
| 2010/0069848 A1 | 3/2010 | Alferness et al. | |
| 2010/0152675 A1 | 6/2010 | McClintock | |
| 2010/0152679 A1 | 6/2010 | Tezel et al. | |
| 2010/0280488 A1 | 11/2010 | Pruitt et al. | |
| 2010/0282774 A1 | 11/2010 | Greter et al. | |
| 2011/0021905 A1 | 1/2011 | Patrick et al. | |
| 2011/0092916 A1 | 4/2011 | Tezel et al. | |
| 2011/0137286 A1 | 6/2011 | Mudd et al. | |
| 2011/0160674 A1 | 6/2011 | Holmes et al. | |
| 2011/0202014 A1 | 8/2011 | Mutzbauer | |
| 2013/0131632 A1 | 5/2013 | Mudd et al. | |
| 2013/0131633 A1 | 5/2013 | Mudd et al. | |
| 2013/0274670 A1 | 10/2013 | Mudd et al. | |

FOREIGN PATENT DOCUMENTS

| | | |
|---|---|---|
| EP | 1486218 | 12/2004 |
| EP | 1859827 | 11/2007 |
| EP | 1923086 | 5/2008 |
| EP | 2335755 | 6/2011 |
| FR | 2622457 | 5/1989 |
| WO | 99/48601 | 9/1999 |
| WO | 2005/095225 | 10/2005 |
| WO | 2008/019265 | 2/2008 |
| WO | 2008/079824 | 7/2008 |
| WO | 2008148071 A2 | 12/2008 |
| WO | 2009003135 A1 | 12/2008 |
| WO | 2009/098666 | 8/2009 |
| WO | 2009/158145 | 12/2009 |

OTHER PUBLICATIONS

Park et al., "Biological characterization of EDC-crosslinked collagen-hyaluronic acid matrix in dermal tissue restoration", Biomaterials, Elsevier Science Publishers BV, vol. 24, No. 9, Apr. 1, 2003, pp. 1631-1641, XP004404219.

Wang et al., "In vivo stimulation of de novo collagen production caused by cross-linked hyaluronic acid dermall filler injections in photodamaged human skin.", Archives of Dermatology, American Medical Association, US, vol. 143, No. 2, Feb. 1, 2007, pp. 155-163, XP002574140.

* cited by examiner

1 = Fat; 2 = Additive (in an alternative embodiment, these could be switched)

SYRINGE FOR MIXING AND DISPENSING ADIPOSE TISSUE

This application claims priority to U.S. Provisional Patent Application No. 61/683,157, filed Aug. 14, 2012 the entire contents of which is incorporated herein by reference.

The present invention generally relates to fat grafting procedures and more specifically relates to devices and methods for combining and dispensing adipose tissue and biocompatible additives for use in fat grafting procedures.

Autologous fat transfer (AFT), also known as fat grafting, is a process by which fat is harvested from one part of a human body and injected into another part of the same person's body where additional bulk may be needed or desired for cosmetic and/or aesthetic purposes. Clinical applications for autologous fat transfer are expanding rapidly with recent reported use in breast reconstruction and augmentation, buttock enhancement, treatment of congenital tissue defects, facial reconstruction, and skin rejuvenation. Although this is a very attractive approach and there is an increased trend in replacement of soft tissue volume with AFT, typical survival rates of grafted fat may be poor and overall results may not be satisfactory.

U.S. Patent Application Publication No. 20110202014 discloses a fat graft syringe assembly for delivering small amounts of fat graft material to treat delicate anatomical areas.

WO 2008148071 discloses kits, tools, and methods are described for harvesting, processing, and using injectable dermis in volume filling procedures.

WO 200903135 discloses system for harvesting fat through liposuction, concentrating the aspirate so obtained, and then re-injecting the concentrated fat into a patient.

There still remains a need for improved devices and methods for use in fat grafting procedures.

SUMMARY

Accordingly, a device for introducing into a target region of a patient, a combination of adipose tissue and an additive, is provided. The device generally comprises a fat cartridge for containing an amount of processed or unprocessed adipose tissue or adipose derived material, and an additive cartridge for containing an additive to be combined with the adipose material. The device further comprises a housing configured to receive, for example, in a side-by-side manner, the fat cartridge and additive cartridge, and a mixing tip on the housing, the mixing tip including a distal end for receiving a cannula or needle. The device further comprises a plunger assembly including a fat cartridge plunger and an additive cartridge plunger, configured to be slidably received in the fat cartridge and the additive cartridge, respectively, and for applying force to the contents of the respective cartridges for moving the contents into the mixing tip and eventually out of the cannula or needle.

In some embodiments, the fat cartridge plunger and the additive cartridge plunger are fixed with respect to each other, for example, at a proximal end of the plunger assembly.

In some embodiments, the housing is configured to receive the fat cartridge and the additive cartridge in a longitudinally slidable manner. In other embodiments, the housing is configured to receive the fat cartridge and the additive cartridge in a lateral manner.

In one aspect of the invention, the device further comprises a mechanism for preventing extrusion of additive from the additive cartridge without coextrusion of fat from the fat cartridge.

In another aspect of the invention, a device is provided for administering a formulation comprising an adipose tissue and an additive wherein the device generally comprises (a) a first cartridge for containing an adipose tissue, (b) a second cartridge for containing an additive to be added to and mixed with the adipose tissue and (c) a housing configured to substantially enclose in a side-by-side manner the first and the second cartridges. In addition, the device comprises (d) a mixing tip on the housing, wherein the mixing tip includes (i) a chamber or lumen, (ii) a proximal end for receiving and conducting into the lumen the adipose tissue and the additive for mixing within the lumen, and (iii) a distal end for receiving a cannula or needle through which the formulation can be administered. Further still, the device may comprise (e) a plunger assembly including a first cartridge plunger and a second cartridge plunger, the plunger assembly configured to be slidably received in the first cartridge and in the second cartridge and the plunger assembly when actuated acting to push the adipose tissue, by the action of the first cartridge plunger, from the first cartridge into the lumen and to push the additive, by the action of the second cartridge plunger, from the second cartridge into the lumen, for the mixing therein.

Each and every feature described herein, and each and every combination of two or more of such features, is included within the scope of the present invention provided that the features included in such a combination are not mutually inconsistent.

BRIEF DESCRIPTION OF THE DRAWINGS

The present invention may be more clearly understood and the advantages thereof better appreciated by considering the below Detailed Description and accompanying Drawings of which.

DETAILED DESCRIPTION

Figure 1:
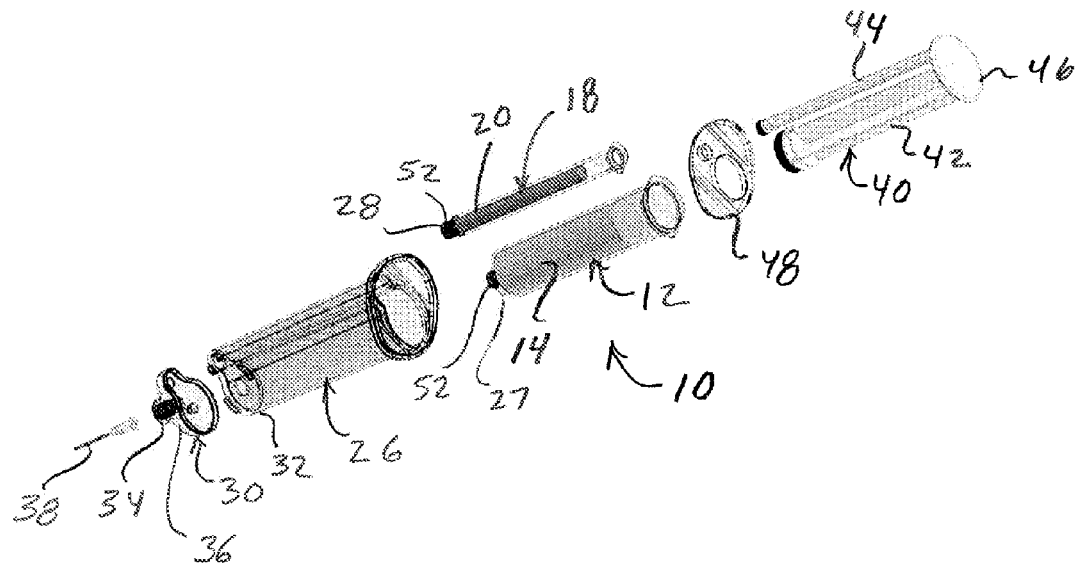
FIG. 1 is a perspective, exploded view of a device in accordance with one embodiment of the invention.
Figure 2:
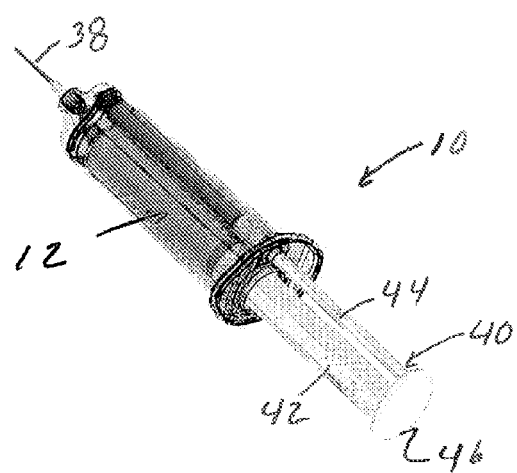
FIG. 2 is a perspective view of the device of FIG. 1, in a fully assembled condition.

Referring now to FIGS. 1 and 2, in the shown embodiment, a dual cartridge syringe device, for injection of fat with an additive into the body is provided. The device 10 is generally structured to mix freshly harvested and/or processed fat with an additive for improved viability as it is injected into a patient, for example, for breast augmentation, body contouring, dermal filling, reconstructive purposes, or the like.

The device 10 generally comprises a first cartridge 12, hereinafter sometimes referred to as a fat cartridge 12, for containing an amount of processed or unprocessed adipose tissue or adipose derived material, and a second cartridge 18, hereinafter sometimes referred to as an additive cartridge 18, for containing an additive 20 to be combined with the adipose tissue 14.

The adipose tissue may be in the form of freshly harvested or processed lipoaspirate, including adipocytes, adipose-derived stem cells, stromal vascular fraction cells, or combinations thereof.

Additives useful in within the scope of the present devices may be any material that may be mixed with cellular material, for example, living cells, for example, adipose tissue including adipose cells, and which is beneficial to maintaining the viability of the cellular material when mixed therewith and then injected or implanted in a body. Such additives may be in the form of hydrogels that enhance, promote or support cell proliferation or survival. Additives useful in the present devices are described, for example, in commonly owned U.S. Provisional Patent Application No. 61/586,589, filed on Jan. 13, 2012, and entitled CROSSLINKED HYALURONIC ACID-COLLAGEN MATRICES FOR IMPROVING TISSUE GRAFT VIABILITY AND SOFT TISSUE AUGMENTATION, and U.S. patent application Ser. No. 13/740,712, filed on Jan. 14, 2013, the entire disclosure of each of these documents being incorporated herein by this reference.

When injected or implanted in vivo, the hydrogel or a hydrogel composition may promote cell and/or tissue growth, including growth into the implant material. For example, a hydrogel or hydrogel composition may stimulate angiogenesis, neovascularization, adipogenesis, collagenesis, cell infiltration, tissue integration, and the like in vivo. Once injected or implanted into a soft tissue using the devices of the present invention, a combined hydrogel composition and fat material may stimulate angiogenesis, neovascularization, adipogenesis, and/or collagenesis. The hydrogel composition may comprise a hyaluronic acid component and a collagen component, for example, a hyaluronic acid component crosslinked to a collagen component.

Turning back now to FIGS. 1 and 2, the device 10 further comprises a housing 26 configured to receive, for example, in a side-by-side manner as shown, the fat cartridge 12 and additive cartridge 18. In some embodiments, the device may be structured such that the additive cartridge 18 is non-removable, or fixed with respect to the housing, as a means to prevent or discourage misuse of the additive.

In the shown embodiment, the fat cartridge 12 and additive cartridge 18 include luer end 27, 28, respectively. The housing is configured to hold two distinct, for example, different, cartridge sizes, as shown. In one embodiment, the volume ratio of fat cartridge to additive cartridge is about 2:1, up to about 5:1. For example, in the shown embodiment, the fat cartridge 12 may be sized to contain between about 5 ml to about 60 ml, or more, of material, and the additive cartridge 18 may be sized to contain between about 1 ml to about 30 ml of material. Other ratios and sizes are contemplated and are considered to be within the scope of the present invention.

The device 10 may further include a tip 30 coupled to or integral with a distal end 32 of the housing 26. The tip 30 generally includes a lumen or chamber 36, a proximal end for receiving and conducting into the lumen 36 the adipose tissue 14 and the additive 20, which may be mixed or combined within the lumen 36. The tip 30 further includes a distal end structured for receiving a cannula or needle, for example, more specifically, a needle hub. Formulation comprising a mixture of adipose tissue and additive may be passed from the tip lumen 36 into the needle or cannula 40 and thereby administered to a patient. The tip 30 includes a distal end 34 for receiving a cannula or needle 40, for example, more specifically, a needle hub. The tip lumen or chamber 36 may be structured to cause mixing or combining of fat and additive as these materials are passed through the chamber 36 and into the cannula or needle 38. Suitable needle and cannula gauges useful in the present invention include, but are not limited to, for example, 14 gauge up to 32 gauge needle/cannulas. Needle/cannulas may be blunt end or sharp.

The device 10 further comprises a plunger assembly 40 including a fat cartridge plunger 42 and an additive cartridge plunger 44, configured to be slidably received in the fat cartridge 12 and the additive cartridge 18, respectively, and for applying force to the contents of the respective cartridges 12, 18 for moving the contents 14, 20 into the tip 30 and eventually out of the cannula or needle 38 and into a patient.

In this shown embodiment, the plunger assembly 40 is a unitary structure, for example, a unitary molded structure, with proximal portion 46 providing a coupling region between fat cartridge plunger 42 and additive cartridge plunger 44. Proximal portion 46 may be configured as a planar surface, a concave or convex surface, to accommodate a thumb of an operator of the device 10. As shown, the plunger assembly 40 may be configured to be slidably received in the first cartridge 12 and in the second cartridge 18 and the plunger assembly 40 when actuated acting to push the adipose tissue 14, by the action of the first cartridge plunger 42, from the first cartridge 12 into the tip lumen 36 and to push the additive 20, by the action of the second cartridge plunger 44, from the second cartridge 18 into the lumen 36, for the mixing therein.

For each fat grafting procedure, the fat cartridge 12 is filled with freshly harvested or processed adipose tissue and placed into or engaged with the housing 26. The additive cartridge 18 is filled with an additive is also placed into the housing 26. A housing top cover 48 is snapped over the two cartridges 12, 18 securing them firmly in place in the housing 26. The tip 30 is snapped onto the housing 26 using a suitable mechanism, for example, o-rings 52, to seal fat cartridge luer end 27 and additive cartridge luer end 28 to the tip 30.

In use, an operator loads the fat cartridge 12 containing freshly harvested and/or prepared fat, into the fat cartridge 12. The additive cartridge 18 may already be in place in the housing 26, or the operator engages the additive cartridge 18 with the housing 26 just prior to the procedure. The housing top cover 48 is snapped into the housing 26 which is engaged to the mixing tip 30. The plunger assembly 40 is inserted into the cartridges 12, 18. The operator places the needle or cannula tip into a target region of the patient and presses the proximal portion 46 of the plunger assembly 40 to cause extrusion of fat and additive into the target region.

In some embodiments, the tip 30 may be modular in that it can be provided in a variety of different configurations allowing for a variety of mixing configurations and requirements. In some embodiments, for example, the tip 30 is configured to include mixing elements such as helical static mixers, grooves, pins, or other structure within the chamber 36 to effect mixing of the fat and additive as these are being extruded through chamber 36.

Figure 3:
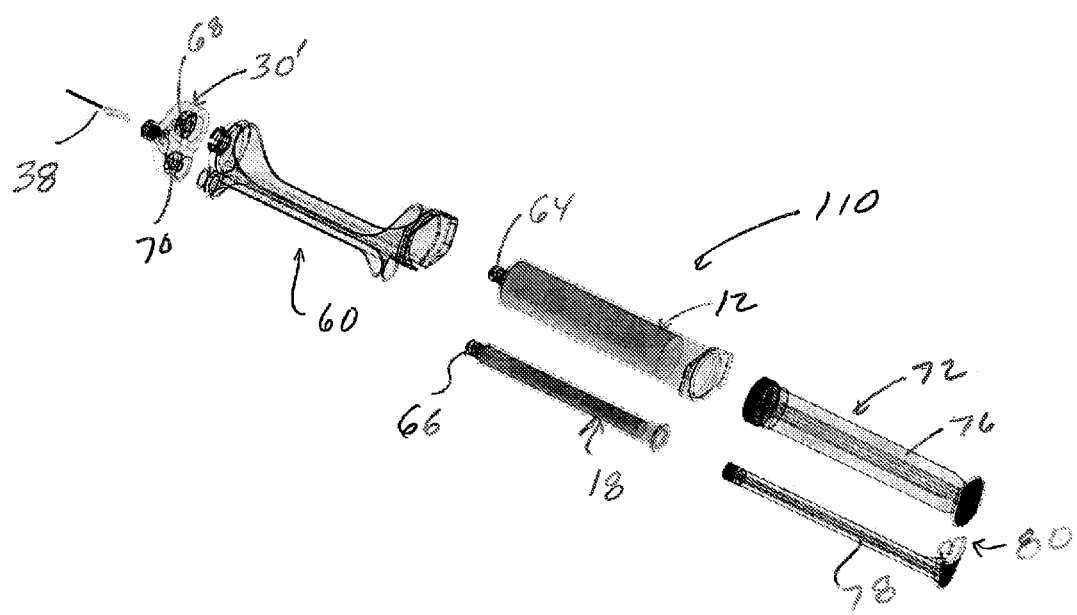
FIG. 3 is a perspective, exploded view of another device in accordance with another embodiment of the invention.
Figure 4:
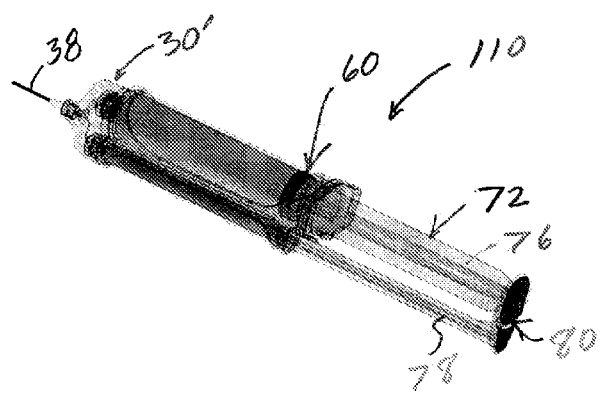
FIG. 4 is a perspective view of the device of FIG. 3, in a fully assembled condition.

Turning now to FIGS. 3 and 4, another embodiment 110 of the present invention is shown.

Device 110 is similar to device 10 shown in FIGS. 1 and 2, with a difference being that instead of housing 26, device 110 includes open sided housing 60 which allows cartridges 12, 18 to be installed to mixing tip 30' by using luer thread or slip connector 64, 66 on cartridges 12, 18, rather than o-ring seals. Mixing tip 30' is similar to tip 30, with a major distinction being that mixing tip 30' includes coupling structure 68, 70 configured to engage luer connectors 64, 66, respectively, of cartridges 12, 18 rather than o-ring seals.

For example, for each surgical procedure, mixing tip 30' is snapped onto the open-sided housing 60. Additive cartridge 18 containing additive is inserted into the housing 60 through proximal end thereof, and is rotated until the luer feature 66 engage and tighten into the corresponding coupling structure 70 on tip 30'. Similarly, the fat cartridge 12 can be inserted into the housing 60 and snapped or rotated in place. The fat cartridge 12 seats into the tip 30' and uses the interference between luer end of the fat cartridge 12 and the corresponding connector 68 of tip 30' for creating a seal therebetween. Needle or cannula 38 may be installed to the tip 30 in a usual manner.

Also shown in FIGS. 3 and 4, is another feature different from the device 10 shown in FIGS. 1 and 2. Rather than plunger assembly 40, device 110 may include a plunger assembly 72 having separate, or separable, fat cartridge plunger and additive cartridge plunger 78 which include coupling structure 80, such as a snap engagement or a slidable engagement, as shown.

Figure 5:
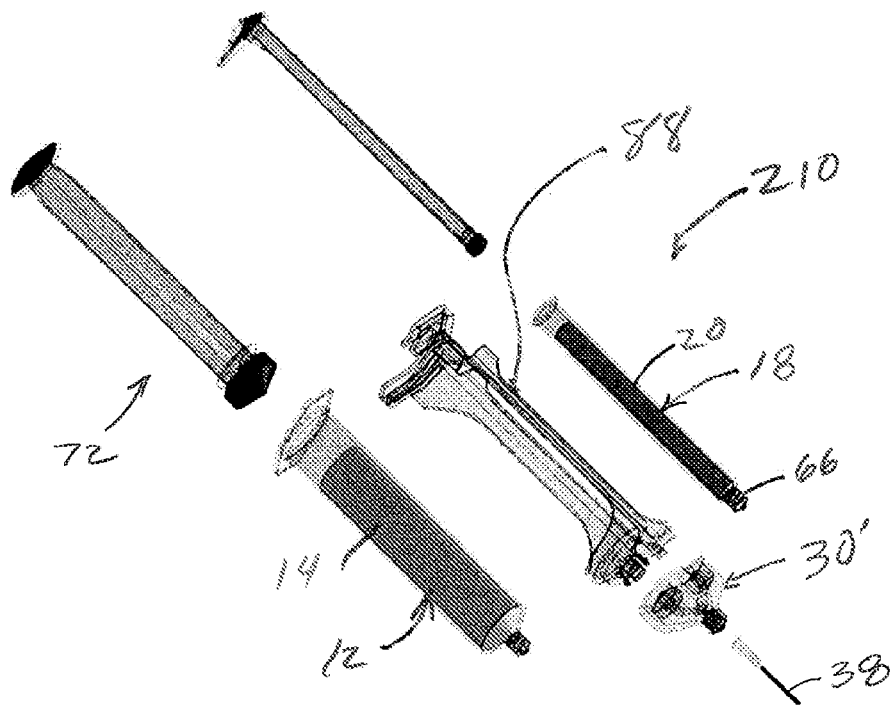
FIG. 5 is a perspective, exploded view of another device in accordance with yet another embodiment of the invention.
Figure 6:
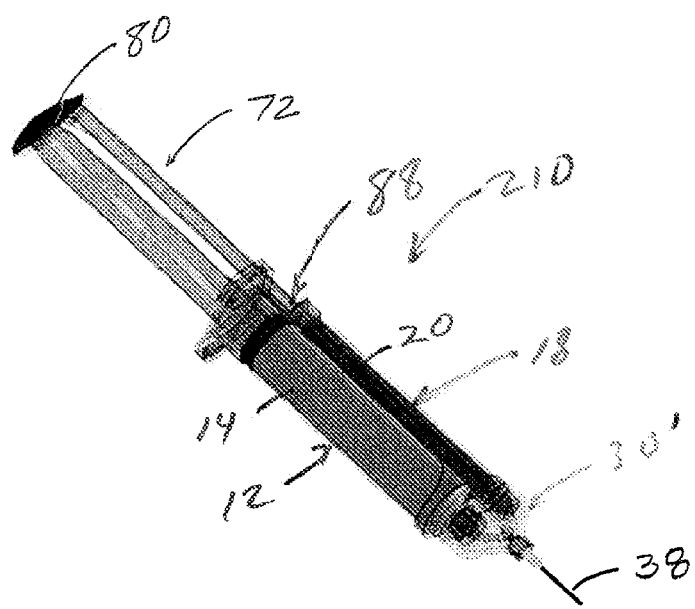
FIG. 6 is a perspective view of the device of FIG. 5, in a fully assembled condition.

Turning now to FIGS. 5 and 6, another embodiment is shown generally at 210. This device 210 is similar to device 110, with a major difference being that instead of open sided housing structured for proximal end loading of cartridges 12, 18, device 210 includes a frame housing 88 which allows for side loading, or lateral loading, of cartridges 12, 18. Other features of this embodiment may be identical or similar to corresponding features of device 110 or 10.

For example, for each surgical procedure, tip 30' is snapped onto the housing 88. Cartridge 18 containing additive 20 is placed into the housing 88 by either snapping the cartridge 18 straight in from the side, or by slipping the luer end 66 into side opening of housing 88, then snapping the proximal end of cartridge 18 into the proximal end of housing 88. The cartridge 18 may then be pressed or rotated until it tightens into the tip 30'. The fat cartridge 12 containing adipose material 14 can then be snapped into the housing 88 in a similar manner. The fat cartridge 12 seats into the tip 30' and uses the interference between the existing luer center protrusions of the fat cartridge and the tip 30' for a seal. Manual pressing of the proximal end 80 of plunger assembly 72 causes extrusion of cartridge contents 14, 20 through needle or cannula 38.

Figure 7:
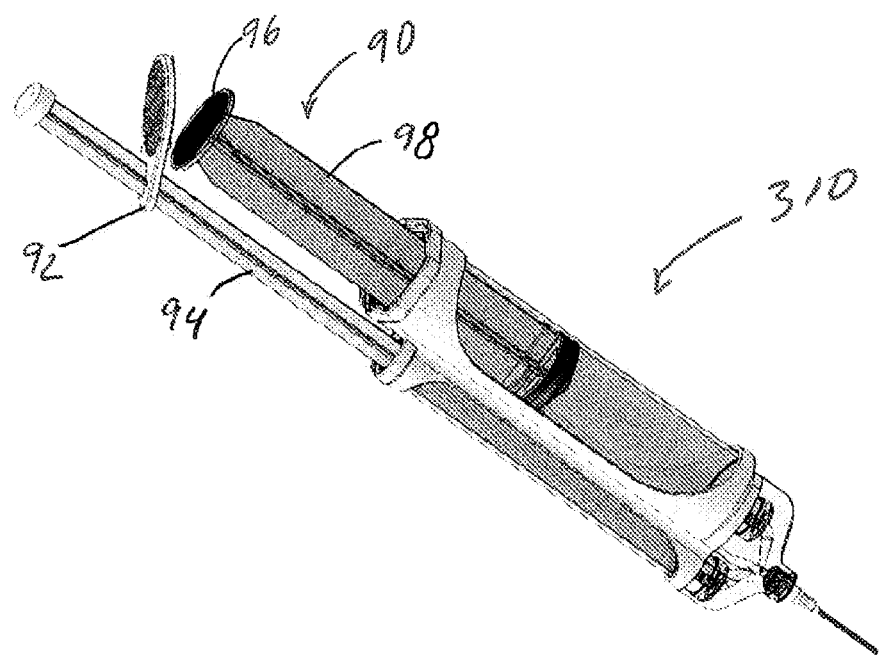
FIGS. 7 and 8 are perspective views of yet another device in accordance with another embodiment of the invention, including an adjustable thumb piece loose for positioning (FIG. 7) and engaged (FIG. 8).
Figure 8:
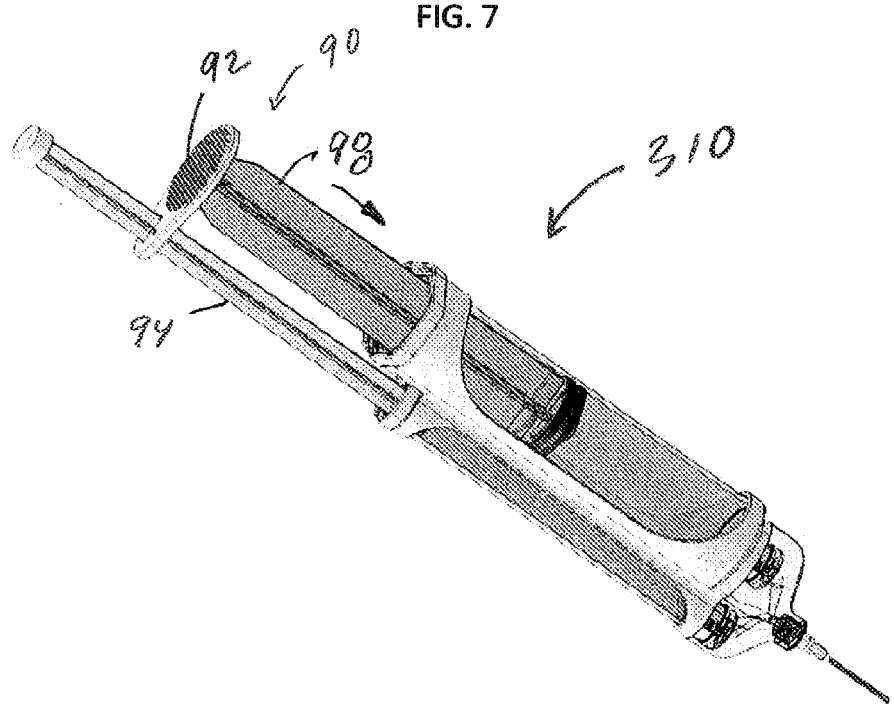

Turning now to FIGS. 7 and 8, another device in accordance with the invention is shown generally at 310. Device 310 includes a plunger rod assembly 90 having structure for allowing variations in the quantity of harvested adipose material 14. For example, plunger rod assembly 90 may include a fat cartridge plunger rod 98, an additive plunger rod 94, and a variable position plunger rod/thumb piece 92 designed to lock the plunger rods 98, 94 together in variable positions. In the shown embodiment, the thumb piece 92 is pivotally coupled to additive plunger rod 94, and engageable with a corresponding fat cartridge plunger proximal portion 96 of fat cartridge plunger rod 98. The fat cartridge plunger rod 98 may be moved to a desired position and the thumb piece 92 may be then engaged to (e.g. snapped onto) the fat cartridge plunger proximal portion 96, thus fixing the fat cartridge plunger rod 98 and additive cartridge plunger rod 94 in place with respect to each other. This arrangement allows a desired volume injection ratio of fat to additive as the plunger assembly 90 to be maintained while thumb piece 92 is depressed and plunger rods 94, 98 move in unison through cartridges 12, 28. (FIG. 8).

Figure 9:
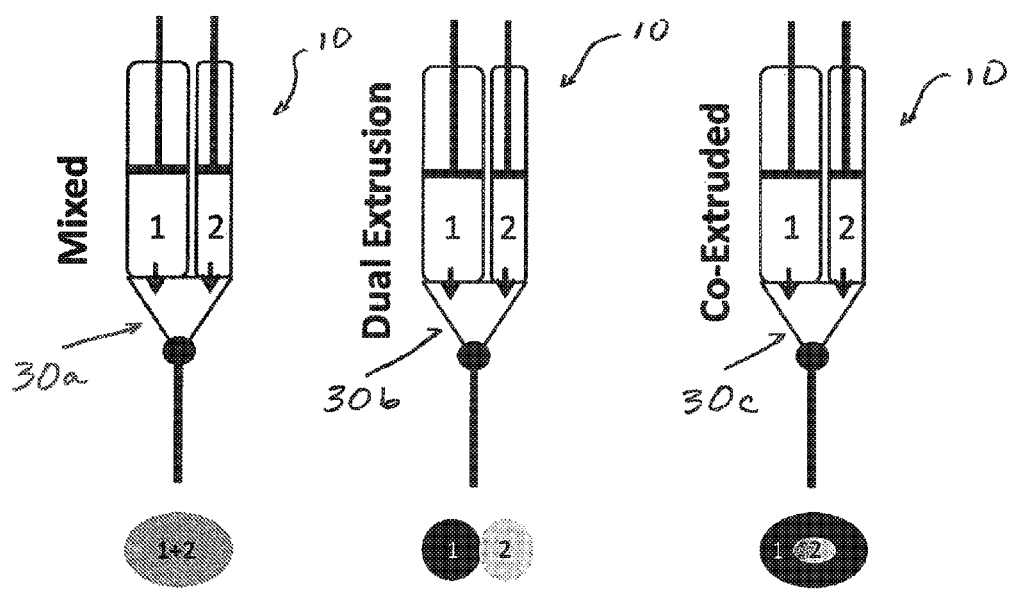
FIG. 9 shows simplified views of a device of the invention including a variety of different mixing tips.

Turning now to FIG. 9, it is contemplated that different tips, for example, tips 30a, 30b, and 30c, may be provided on the device 10 (or 110, 210 or 310) of the invention for providing different extrusion/mixing results. Each of these tips 30a, 30b and 30c may serve unique benefits, such as improved vascularization of the fat, decreased extrusion force (for usability), as may be beneficial for different applications on the body.

For example, tip 30a may be provided which includes suitable structure effective to mix or combine the fat material 1 with the additive 2 as these materials 1, 2 are passed through tip 30a immediately prior to extrusion from needle or cannula 38. Alternatively, tip 30b may be provided which is structured to extrude fat material 1 and additive 2 without substantial or significant mixing. Alternatively still, tip 30c may be provided which is structured to provide a co-extrusion of fat material 1 and additive 2, as shown. Although not shown, it can be appreciated that tip 30c may be configured to provide a coextrusion with fat 1 surrounded by additive 2, rather than as shown (additive 2 surrounded by fat 1).

Other tips and structure useful as components of the present devices 10, 110, 210, 310 are disclosed in U.S. patent application Ser. No. 12/909,216, filed on Oct. 21, 2010, and entitled DUAL CARTRIDGE MIXER SYRINGE, the entire disclosure of which is incorporated herein by this specific reference.

In another aspect of the invention, the device 10, 110, 210, 310 may include a mechanism for discouraging or preventing tampering or misuse of product.

For example, as mentioned hereinabove, the additive cartridge may be permanently fixed in the housing to prevent removal without destruction of the device.

Figure 10:
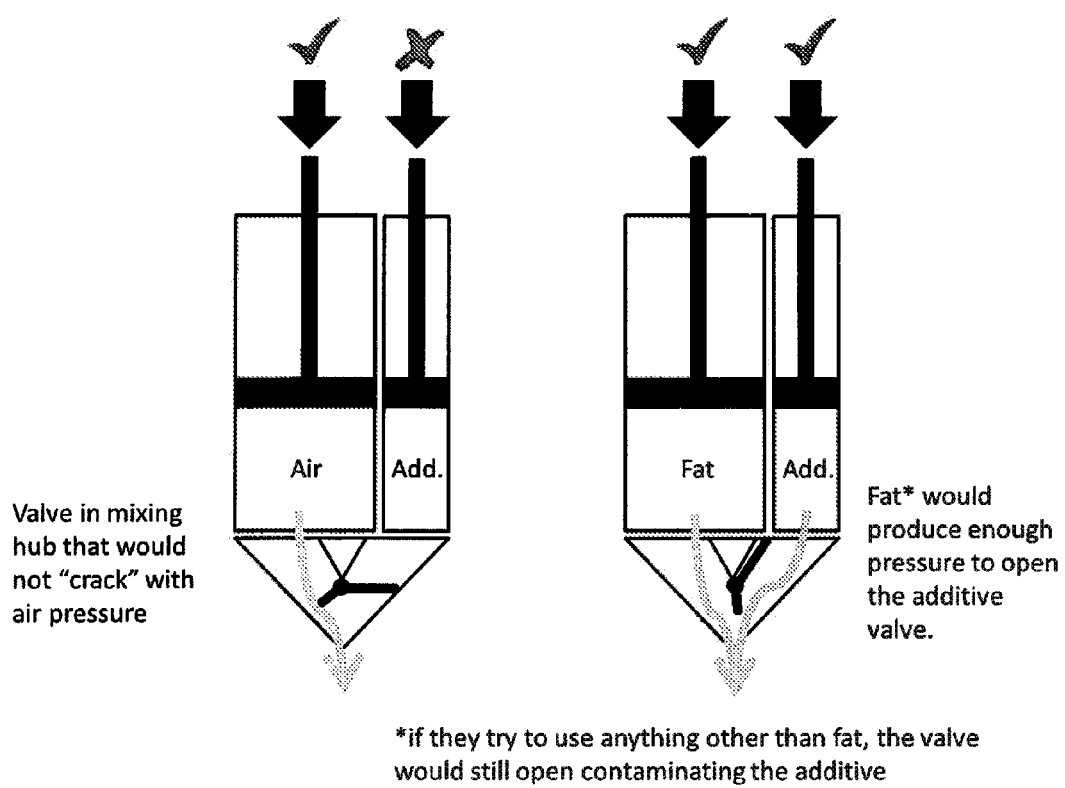
FIG. 10 is a simplified diagram of a feature of the invention for preventing misuse thereof.

Alternatively or additionally, as illustrated in FIG. 10, a feature may be provided which reduces, eliminates or prevents a user from extruding or removing the additive from the device, without also extruding fat material therewith.

For example, the tip 30 or 30' may be provided with a valve 104. Valve 104 includes geometry that allows opening of the additive injection channel only when engineered pressures are induced. Typically air, a highly compressive medium is unable to create a sufficient spike in pressure to rotate the valve and allow dispensing of additive. Alternatively, a medium like fat, a non-compressive medium, is able to create the pressure spike and rotate the valve for additive injection. In other embodiments, the valve could involve flaps, diaphragms, pinches, or other means to achieve the same function. Valve 104 is structured to remain sealed or closed in the event that only air pressure is applied to the fat cartridge valve seat. Thus, the valve 104 would prevent dispensing of additive alone.

While this invention has been described with respect to various specific examples and embodiments, it is to be understood that the invention is not limited thereto and that it can be variously practiced within the scope of the invention.

What is claimed is:

1. A device for introducing into a target region of a patient, a combination of adipose tissue and an additive, the device comprising:
    a fat cartridge;
    an additive cartridge;
    a housing configured to receive, in a side-by-side manner, the fat cartridge and additive cartridge;
    a mixing tip on the housing, the mixing tip including a distal end for receiving a cannula or needle;
    a plunger assembly slidably received in the fat cartridge and the additive cartridge, the assembly including a fat cartridge plunger rod and an additive cartridge plunger rod;
    a thumb piece structured to fix the fat cartridge plunger rod and the additive cartridge plunger rod in place, in variable positions, with respect to each other; and a valve structured to prevent extrusion of additive from the additive cartridge without extrusion of fat from the fat cartridge.

2. The device of claim 1 wherein the thumb piece is structured to be snapped onto the fat cartridge plunger rod.

3. The device of claim 1 wherein the housing is configured to receive the fat cartridge and the additive cartridge in a longitudinally slidable manner.

4. The device of claim 1 wherein the housing is configured to receive the fat cartridge and the additive cartridge in a lateral manner.

5. The device of claim 1 wherein the additive cartridge contains an additive.

6. The device of claim 5 wherein the additive comprises hyaluronic acid and collagen.

7. The device of claim 5 wherein the additive comprises hyaluronic acid crosslinked with collagen.

8. A device for introducing into a target region of a patient, a combination of adipose tissue and an additive, the device comprising:

a fat cartridge;

an additive cartridge including an additive;

a housing configured to receive, in a side-by-side manner, the fat cartridge and additive cartridge;

a mixing tip on the housing, the mixing tip including a distal end for receiving a cannula or needle;

a plunger assembly slidably received in the fat cartridge and the additive cartridge, the assembly including a fat cartridge plunger rod and an additive cartridge plunger rod;

a thumb piece structured to fix the fat cartridge plunger rod and the additive cartridge plunger rod in place, in variable positions, with respect to each other; and a valve structured to prevent extrusion of additive from the additive cartridge without coextrusion of fat from the fat cartridge.

9. The device of claim 8 wherein the additive comprises hyaluronic acid crosslinked with collagen.

\* \* \* \* \*

UNITED STATES PATENT AND TRADEMARK OFFICE
CERTIFICATE OF CORRECTION

PATENT NO. : 9,095,654 B2  Page 1 of 1
APPLICATION NO. : 13/966953
DATED : August 4, 2015
INVENTOR(S) : Justin Schwab et al.

It is certified that error appears in the above-identified patent and that said Letters Patent is hereby corrected as shown below:

Title Page, item (56)

On the Page 2, in column 2, under "Other Publications", line 3, delete "Publishiers" and insert -- Publishers --, therefor.

On the Page 2, in column 2, under "Other Publications", line 6, delete "dermall" and insert -- dermal --, therefor.

In the Specification

In column 3, line 1, delete "tissue" and insert -- tissue 14 --, therefor.

In column 3, line 46-47, delete "housing" and insert -- housing 26 --, therefor.

In column 5, line 19, delete "plunger and" and insert -- plunger 76 and --, therefor.

Signed and Sealed this
Fifteenth Day of March, 2016

Michelle K. Lee
*Director of the United States Patent and Trademark Office*